United States Patent [19]

Bergmann

[11] Patent Number: 5,541,116
[45] Date of Patent: Jul. 30, 1996

[54] METHOD FOR THE STABILIZATION OF ENDOGENOUS, PHYSIOLOGICALLY ACTIVE PEPTIDES

[75] Inventor: Andreas Bergmann, Berlin, Germany

[73] Assignee: B.R.A.H.M.S. Diagnostica GmbH, Berlin, Germany

[21] Appl. No.: 66,156

[22] PCT Filed: Aug. 13, 1991

[86] PCT No.: PCT/EP92/01855

§ 371 Date: Oct. 1, 1993

§ 102(e) Date: Oct. 1, 1993

[87] PCT Pub. No.: WO93/07489

PCT Pub. Date: Apr. 15, 1993

[30] Foreign Application Priority Data

Sep. 30, 1991 [DE] Germany ................. 41 32 587.7

[51] Int. Cl.⁶ .................... G01N 1/28; G01N 33/68; G01N 33/543
[52] U.S. Cl. .................... 436/176; 435/7.1; 435/24; 435/963; 436/518; 436/536; 436/8; 436/826
[58] Field of Search .................... 436/518, 8, 17, 436/18, 176, 804, 825, 826, 536; 435/7.1, 24, 962, 963, 967, 975

[56] References Cited

U.S. PATENT DOCUMENTS

| | | | |
|---|---|---|---|
| 5,015,627 | 5/1991 | Lindsey et al. | 514/12 |
| 5,039,446 | 8/1991 | Estell | 252/174.12 |
| 5,096,811 | 3/1992 | Hotchkiss et al. | 435/23 |
| 5,168,041 | 12/1992 | Bergmann | 435/7.1 |

FOREIGN PATENT DOCUMENTS

| | | |
|---|---|---|
| 0306167 | 3/1989 | European Pat. Off. |
| 0336779 | 10/1989 | European Pat. Off. |
| 0362773 | 4/1990 | European Pat. Off. |
| 0385488 | 9/1990 | European Pat. Off. |
| 0397409 | 11/1990 | European Pat. Off. |
| 0286367 | 7/1992 | European Pat. Off. |
| 8909233 | 10/1989 | WIPO |
| 9012029 | 10/1990 | WIPO |

OTHER PUBLICATIONS

Yalow et al, 1971. "Problems of validation of radioimmunoassays" in *Pri ciples of Competitive Protein–Binding assays* (W. D. Odell et al, eds). J B Lippincott, Philadelphia pp. 374–375, 379, 381.
Franchimont et al, 1983. "Pitfalls in peptide radioimmunoassays" in *Principles of Competitive Protein–Binding Assays* (W. D. Odell et al, eds.) John Wiley & Sons, New York, pp. 149–151.
Zaidi et al, 1991. Expression and function of the calcitorin gene productsion. Vitamins and Hormones, vol. 46, Adv in Res. and Applic. p. 98.
Gibson et al, 1989. Advantages of IRMA over RIA in the measurement of ACTH. Ann Clin Biochem 26:500–507.
Pharmacological Reviews vol. 30, No. 3, pp. 247–292 (1978), H. Bennett et al. "Peptide Hormones and Their Analogues: Distribution, Clearance from the Circulation, and Inactivation in Vivo".
Biochem. Biophys. Res. Commun. vol. 118, pp. 131 (1984), K. Kangawa et al. "Purification and complete amino acid sequence of α-human atrial natriuretic polypeptide (α-hANP)".
Life Sci. vol. 36, pp. 2171 (1985), M. Marin–Grez et al. "Dopamine receptor antagonists inhibit the natriuretic response to atrial natriuretic factor (ANF)".

*Primary Examiner*—Christina Y. Chan
*Assistant Examiner*—James L. Grun
*Attorney, Agent, or Firm*—Cushman Darby & Cushman, LLP

[57] ABSTRACT

Method for the stabilisation of endogenous physiologically active peptides in human whole blood, serum and plasma samples before and/or during the determination of the concentration of these peptides by immunodiagnostic or physical assay methods, in which a stabiliser combination which consists of the protease inhibitors amastatin and leupeptin and ethylenediaminetetraacetic acid (EDTA) or contains the stated compounds is added to the samples.

6 Claims, No Drawings

METHOD FOR THE STABILIZATION OF ENDOGENOUS, PHYSIOLOGICALLY ACTIVE PEPTIDES

The invention relates to a method for the stabilisation of endogenous, physiologically active peptides in human whole blood, serum or plasma samples before and/or during the determination of the concentration of these peptides by immunodiagnostic or physical assay methods.

Peptides have important biological functions as hormones and biomodulators. Owing to their high biological activity, their half-life in the body is very limited, and the various physiologically active peptides have different deactivation and degradation mechanisms corresponding to the biological function of these peptides. A review of a number of physiologically important peptides or peptide hormones and their deactivation in the human body is to be found, for example, in the article by Hugh P. J. Bennett and Colin McMartin in Pharmacological Reviews, Vol. 30, No. 3, pages 247 to 292. This article states that the half-life of peptides in the blood is influenced by many different factors, including the absorption or binding by the tissue, degradation by specific tissue regions or organs and degradation or conversion in the blood or plasma.

If it is intended to determine the concentration of such short-lived peptides in the blood of experimental animals or in particular of human patients, this short life must be borne in mind and if necessary countermeasures taken.

To determine the concentration of biological molecules, such as peptides, in the blood, it is first necessary to take a blood sample, from which a serum sample or plasma sample is then obtained in a known manner and is then used in the assay method for determining the concentration of the particular biological molecule. Although the concentration of various biological molecules may also be measured by means of physical methods, such as chromatographic methods, spectroscopic methods or separation, such as dialysis or ultrafiltration, biological molecules in the blood are as a rule measured by means of various immunodiagnostic methods, owing to the small amounts in which they occur and owing to the high accuracy of determination required in clinical investigations. In these methods, the serum sample or plasma sample, together with the further substances required for the particular immunodiagnostic method (labelled or unlabelled, suspended or immobilised antibodies, labelled tracer molecules, buffer) are incubated with one another for a certain time.

Usually, a considerable time elapses between taking of the sample and obtaining serum or plasma samples and the actual measurement of biological molecules. In the case of sensitive endogenous peptides, however, endogenous biological degradation of the peptides in the sample may occur in the period between taking of the sample or sample preparation and the actual determination, and the endogenous biological degradation of the peptides may continue even during the period of incubation of the sample during the assay procedure, so that, depending on the degree of degradation, the assay method measures not the required physiological peptide concentration which was present at the time of blood withdrawal but another peptide concentration whose magnitude is dependent on the method and duration of storage, the serum plasma isolation and the incubation. If only the complete, undegraded peptide is recognised in the assay method, values which are too low are therefore obtained. There are, however, immunodiagnostic assay methods in which possible degradation products of a certain peptide are better recognised than the peptide itself, so that, in the case of degradation of the required peptide, concentrations which are higher than the actual concentrations may be measured.

However, incorrect measurements may lead to incorrect clinical interpretations of the measurements.

In order to counteract the danger of the degradation of endogenous peptides, which has been known in principle for a long time, attempts are known to have been made to prevent such degradation by the presence of EDTA or of individual proteolysis inhibitors. It is also known that the peptides can be stabilised by immediate freezing of the samples or by freeze-drying of the samples. It is furthermore known that the degradation of the peptides to be determined can be reduced by a so-called heat treatment, proteases responsible for a proteolytic degradation being deactivated.

Although in principle it is assumed that proteolytic degradation is involved in the degradation of endogenous peptides, as a rule it is not known to date how this degradation takes place specifically and how it can be effectively suppressed for a specific endogenous peptide in the serum/plasma.

Physiologically active endogenous peptides which have only a limited life or possible candidates for proteolytic degradation in blood, serum or plasma samples are, for example, the adrenocorticotropic hormone (corticotropin, ACTH), the angiotensins, the atrial peptides, including atrial natriuretic peptide (ANP), bradykinin, calcitonin, calcitonin precursors and the calcitonin gene-related peptide, cholecystokinin, glucagon, interleukins, insulin, katacalcin (PDN-21), luteinizing hormone-releasing hormone (LHRH) and parathormone or parathyroid hormone (PTH).

The present invention concentrates on the stabilisation of the unstable peptides ACTH (adrenocorticotropic hormone) and ANP (atrial natriuretic peptide).

The structure of these two peptides is known and is shown below:

Human ACTH (1-39)     SEQ ID NO:1
Ser—Tyr—Ser—Met—Glu—His—Phe—Arg—Trp—Gly—Lys—Pro—Val—
Gly—Lys—Lys—Arg—Arg—Pro—Val—Lys—Val—Tyr—Pro—Asn—Gly—
Ala—Glu—Asp—Glu—Ser—Ala—Glu—Ala—Phe—Pro—Leu—Glu—Phe Human ANP (1-28)     SEQ ID NO:2
Ser—Leu—Arg—Arg—Ser—Ser—Cys—Phe—Gly—Gly—Arg—Met—Asp—
Arg—Ile—Gly—Ala—Gln—Ser—Gly—Leu—Gly—Cys—Asn—Ser—Phe—
Arg—Tyr (with a disulfide bond between the two Cys residues)

The structures shown have been published in K. Kangawa and H. Matuso; Biochem. Biophys. Res. Commun. 118, 131 (1984) and M. Marin-Grez et al., Life Sci. 36, 2171 (1985).

The two peptides hACTP and hANP differ from one another, both with regard to their size and their structure (ANP is, for example, a cyclic peptide) and with regard to their amino acid sequence, to such an extent that in the present invention it is assumed that a stabilisation method which is similarly effective for both peptides in serum samples and plasma samples can also be suitable for the stabilisation of all or at least many further endogenous, physiologically active peptides.

It is the object of the present invention to provide a method by means of which the endogenous, physiologically active peptides in human whole blood and in particular human serum and plasma samples can be stabilised so that their concentration is not changed, before or during the determination, by degradation which falsifies the measurements.

This object is achieved by a method for the stabilisation of endogenous, physiologically active peptides in human whole blood, serum or plasma samples before and/or during the determination of these peptides by immunodiagnostic or physical assay methods, which is characterised in that a stabiliser combination which consists of the protease inhibitors amastatin and leupeptin and ethylenediaminetetraacetic acid (EDTA) or contains the stated compounds, for example in the form of a solution in a suitable buffer, is added to the samples.

It was furthermore found that the components of the stabiliser combination of the particular sample, in particular serum or plasma sample, must usually be added in amounts such that minimum concentrations of 4 mM EDTA, 25 µM amastatin and 50 µM leupeptin are contained in the particular sample.

The method according to the invention is described in detail in the present invention in particular with regard to the determination of human ACTH in serum and plasma samples and with regard to its realisation by means of a corresponding kit.

In view of the fact that a combination of leupeptin and amastatin is used for peptide stabilisation, the method according to the invention has a certain similarity to the Applicant's method, which is described in its German Patent 38 33 936. However, the method described in the stated patent relates not to the stabilisation of any endogenous peptide to be measured but to the stabilisation of a certain, synthetically prepared oligopeptide tracer which is added in a typical immunoassay in which the substance to be determined and a tracer compete with one another for a substoichiometric amount of antibody. As a result of the addition of a combination of leupeptin and amastatin, it is possible to avoid degradation of this oligopeptide tracer while the determination is being carried out, said degradation falsifying the measurements.

The stated patent gives no indication that the combination of leupeptin and amastatin which is used for stabilising the oligopeptide tracer might also be suitable in connection with the stabilisation of other peptides or would also be effective for stabilisation of the peptides to be determined in the stated patent. Instead, it was extremely surprising when it was found, in connection with the provision of the present invention, that a mixture of leupeptins and amastatin stabilises very different endogenous peptides in blood samples and in particular in serum and plasma samples when EDTA is also present as a third component, and that evidently the stated stabiliser mixture is effective in eliminating the substances which are responsible for the degradation of most endogenous peptides in such samples.

The present invention is illustrated in detail below with reference to Examples.

EXAMPLE 1

For the determination of the degradation of the peptides hACTH 1-39 and hANP 1-28 in human serum or human plasma in the presence of various substances known to be protease inhibitors, ACTH radioiodinated with $^{125}$I and correspondingly radioiodinated $^{125}$I-ANP 1-28 were incubated with serum and plasma and thus exposed to degradation by endogenous proteases which are active in human serum and plasma. After certain time intervals, the reaction mixture was analysed chromatographically in each case by means of reversed-phase HPLC, the result of the chromatography being continuously measured with a radioactivity detector. The starting substances (t=0) are eluted as symmetrical radioactive peaks. Resulting degradation products give, inter alia, further radioactive peaks. The percentage degradation of the starting substances is obtained from the peak integral of the product or of the products divided by the sum of the peak integrals of unchanged starting material and all products times 100.

In a controlled experiment, the normal degradation of the starting peptides is measured, and then the measurement is repeated under identical conditions in the presence of different potential proteolysis inhibitors.

To measure the degradation or the influence of different potential inhibitors, the following procedure was adopted:

$^{125}$I-ACTH or $^{125}$I-ANP (1.5 mio cpm) in 20 µl of phosphate buffer (250 mM, pH 7.4) were mixed with 5 µl of the particular inhibitor solution to be tested, in 15-fold concentration (controls were mixed with 5 µl of water). The reaction was then started by adding 50 µl of freshly obtained serum or EDTA plasma. After the addition, the batches were each incubated at 22° C. (ACTH in serum for 18 h, ACTH in plasma for 25 h, ANP in serum for 1 h and ANP in plasma for 3 h). The reactions were stopped by freezing the samples. Immediately before the chromatographic HPLC analysis, the samples were thawed, 1 ml of the mobile phase A described below was added and the samples were sterile-filtered through 0.2 µm filters and were separated by HPLC using a µ-Bondapack C18 column (0.4×30 cm) from Waters.

The elution of the substances was carried out using a gradient which was produced from a mobile phase A (LMA) of acetonitrile:water:trifluoroacetic acid in a volume ratio of 5:95:0.1 and a mobile phase B (LMB) of acetonitrile:water:trifluoroacetic acid in a volume ratio of 90:10:0.1, as follows:

In 45 minutes linearly from 95:5 (v/v LMA/LMB) (starting conditions) to 65:35 LMA/LMB. The flow rate was 5 ml/min. The radioactivity of the column eluate was monitored continuously by means of a radioactivity monitor (from Raytest). The degradation of the radioactive peptides (in % conversion) was determined from the resulting degradation pattern and with the use of a computer program (Raytest).

It was found that the peptides used in the degradation experiments could be separated from a large number of their fragments during their investigation by HPLC, so that the degradation of the peptides could easily be investigated. Without the addition of proteolysis inhibitors or with the addition of unsuitable proteolysis inhibitors, 35 to 70% degradation of the labelled peptide used was observed at 22° C. under the stated conditions after corresponding incubation with serum or plasma.

The inhibitors used in the experiments were all commercial products. They are listed below together with their particular source (in parentheses): EDTA (Fluka 03610), DPFP (Serra 77205), PMSF (Merck 7349), CCPS (Sigma C-4503), NEM (Serra 11331), bestatin (Novabiochem A02341), amastatin (Biomol 50360), pepstatin (Serra 52682), elastatinal (Sigma E-0881), leupeptin (Biomol 12136), phosporamidone (Novabiochem A01239), benzamidine (Sigma B-6505), trasylol or aprotinin (Sigma A-6012), heparin (Serra 63036), soybean trypsin inhibitor (Sigma T-900) and antithrombin III (Sigma A-7388).

The results obtained are summarised in Table 1 below.

The peptides investigated were obtained from: hACTH (Bachem PACT100) and hANP (Novabiochem 05-23-0300).

TABLE 1

Effect of various protease inhibitors on the hydrolysis of $^{125}$I-ACTH 1–39

| Inhibitor | Concentration | % of hydrolysis rate of the control | |
|---|---|---|---|
| | | in serum | in EDTA plasma |
| Control | / | 100 | 100 |
| Ethylenediamine-tetraacetate | 10 mM | 30 | / |
| Diisopropyl fluorophosphate | 1 mM | 83 | 95 |
| Phenylmethylsulphonyl fluoride | 2 mM | 97 | 100 |
| p-Choloromercury-phenylsulphonic acid | 1 mM | 94 | 62 |
| N-Ethylmaleimide | 2 mM | 48 | 54 |
| Bestatin | 1 mM | 44 | 27 |
| Amastatin | 100 µM | 17 | 3 |
| Pepstatin | 100 µM | 105 | 79 |
| Elastatinal | 100 µM | 97 | 100 |
| Leupeptin | 1 mM | 41 | 27 |
| Phosphoramidone | 1 mM | 98 | 85 |
| Benzamidine | 1 mM | 84 | 80 |
| Trasylol | 2.5 units/ml | 78 | 62 |
| Heparin | 5 mg/ml | 126 | 103 |
| Trypsin inhibitor (soybean) | 0.1 mg/ml | 78 | 71 |
| Antithrombin III | 0.1 unit/ml | 107 | 79 |
| Leupeptin Amastatin | 1 mM + 100 µM | 14 | 0 |
| Leupeptin Amastatin EDTA | 1 mM + 100 µM + 10 mM | 0 | 0 |

The described investigation using $^{125}$I-ACTH 1-39 shows that a combination of leupeptin/amastatin/EDTA completely suppressed the hydrolysis of the serum, whereas in an EDTA-containing plasma the same effect was achieved by the addition of leupeptin and amastatin alone.

The Table furthermore shows that, remarkably, inhibitors which belong to the same inhibitor type, for example are aminopeptidase inhibitors like amastatin, are ineffective or very much less effective.

In view of the results obtained for $^{125}$I-ACTH, the influence of the most effective inhibitor concentration was also investigated with regard to the degradation of $^{125}$I-ANP 1-28. The results are summarised in Table 2.

TABLE 2

Effect of protease inhibitors on the hydrolysis of $^{125}$I-ANP 1–28

| Inhibitor | Concentration | % of hydrolysis rate of the control | |
|---|---|---|---|
| | | in serum | in EDTA plasma |
| Control | / | 100 | 100 |
| Leupeptin Amastatin | 1 mM + 100 µM | / | <10 |
| Leupeptin Amastatin EDTA | 1 mM + 100 µM + 10 mM | <10 | <10 |

Table 2 shows that a mixture of amastatin, leupeptin and EDTA not only stabilises ACTH in the serum or plasma but also just as effectively stabilises the cyclic peptide ANP which has a very different composition.

To determine the concentrations of the individual inhibitors which are required for adequate protection of the peptides, in the presence of the other inhibitors, the concentrations were repeatedly varied. It was found that, for effective protection, the minimum concentrations present in the sample were about 4 mM for EDTA, about 25 µM for amastatin and 50 µM for leupeptin.

Practical Use Example (hACTH Kits)

The practical use of the Applicant's method according to the invention for immunometric assays for the determination of ACTH is illustrated below by an example.

A kit for carrying out an immunoradiometric assay method for ACTH (DYNO®test ACTH from Henning Berlin, prepared for market launch) contains the following components typical for a kit of the present type:

a. The tracer in the form of $^{125}$I-anti-ACTH (34-39) antibody (mouse, monoclonal), a 10 ml red bottle, concentrate which must be reconstituted with 23 ml of tracer buffer before use.

b. The tracer reconstitution buffer, a 23 ml bottle, ready-to-use.

c. Coated tubes, coated with immobilised anti-ACTH (25-21) antibody (mouse, monoclonal), two lots of 50 each, ready-to-use.

d. Wash solution, two 11 ml bottles, concentrate. The content of each bottle is made up to the final volume of 550 ml with distilled water before use.

e. ACTH zero standard (human serum), one 10 ml bottle, ready-to-use.

f. 1 to 6 ACTH standards, intact human ACTH (1-39), in 6 bottles, freeze-dried. The concentrations are 5, 15, 50, 150, 500 and 1500 pg/ml. The standards must be reconstituted with, 1 ml of zero serum each before use.

i,ii. Control sera I and II (human serum), 2 bottles, freeze-dried.

The kit also contains a buffer A which contains the protease inhibitors for inhibiting the ACTH degradation in freeze-dried form and must be dissolved before use in 11 ml of a buffer B, which is likewise included.

To prevent the degradation of ACTH before or during the actual determination, as a first step of the method the solution obtained by mixing the freeze-dried buffer A with the liquid buffer B is transferred to the particular test tubes for the standards and patient sera, i.e. the stabilising buffer is taken, and the ACTH-containing components are stabilised from the outset during the test by buffer A.

Measurement is then carried out in a manner known per se, by incubating the sera or standards in the coated tubes, then adding a wash solution and carrying out a solid/liquid separation and, if necessary, repeating this step, after which the labelled antibody in a suitable buffer is added in a further test step in order to label the ACTH molecules bound to the solid phase. After incubation, a solid/liquid separation and washing are complete, the bound radioactivity is measured and the hACTH concentration in the particular sample is determined therefrom, taking into account the values obtained for the standard.

Instead of the radiolabelled tracer antibody in the immunoradiometric assay described above, in another substantially similar immunoluminescence assay a luminescence-labelled anti-hACTH (34-39) antibody (monoclonal, mouse), for example one labelled with an acridiniumderivative, is used in the corresponding kit (LUMI®test ACTH from Henning Berlin, prepared for market launch). In this case too, the buffer solution containing inhibitors is placed in a test tube before a patient sample or a standard is added.

In conventional practice, in the above cases the patient samples which cannot be used in the determinations immediately after half an hour must be frozen and must be stored at at least −20° C. and must be further processed immediately after thawing.

However, it is also possible in principle to stabilise the patient samples immediately after they have been obtained, by adding an adequate amount of the stabiliser combination according to the invention. For this purpose, the particular physician taking the sample can be provided with a special kit which contains all substances required for sample stabilisation.

adding a stabiliser combination comprising an amount sufficient to prevent degradation of ACTH or ANP of amastatin, leupeptin and EDTA to the sample suspected of comprising ACTH or ANP.

2. The method of claim 1 wherein the sample comprises human whole blood, and wherein the stabiliser combination is added immediately to the sample after obtaining the sample from a patient, and comprising the further step of isolating serum or plasma from the human whole blood sample.

3. The method of claim 1 wherein the stabiliser combination is added to the sample immediately after thawing, wherein the sample had been frozen and then thawed.

4. The method of claims 1, 2 or 3 wherein the assay is an immunodiagnostic assay.

5. The method of claims 1, 2 or 3 wherein the minimum concentrations of the stabiliser combination in the sample

I claim:

1. A method for stabilising ACTH (adrenocorticotropin hormone) or ANP (atrial natriuretic peptide) in a sample, wherein the sample comprises human whole blood, serum or plasma, before and/or during an immunodiagnostic or physical assay to determine the concentration of ACTH and/or ANP in the sample, comprising the step of:

are about 4mM EDTA, about 25 μM amastatin and about 50 μM leupeptin.

6. The method of claim 1 wherein the concentration of ACTH in the sample is to be determined by an immunometric assay employing labelled anti-ACTH antibodies.

* * * * *

UNITED STATES PATENT AND TRADEMARK OFFICE
CERTIFICATE OF CORRECTION

PATENT NO.    :    5,541,116
DATED         :    July 30, 1996
INVENTOR(S)   :    BERGMANN It is certified that errors appear in the above-identified patent and that said Letters Patent is hereby corrected as shown below:

On title page, item [22] should read
as follows:

[22]     PCT Filed:  Aug. 13, 1992

Please correct item [73] on the face of the patent to read as follows:

[73]    Assignee:  B.R.A.H.M.S Diagnostica GmbH,
                            Berlin, Germany Signed and Sealed this Third Day of December, 1996

Attest:

BRUCE LEHMAN

*Attesting Officer*        *Commissioner of Patents and Trademarks*

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 39 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:1:

```
Ser Tyr Ser Met Glu His Phe Arg Trp Gly Lys Pro Val Gly Lys Lys
 1               5                  10                    15

Arg Arg Pro Val Lys Val Tyr Pro Asn Gly Ala Glu Asp Glu Ser Ala
            20                  25                  30

Glu Ala Phe Pro Leu Glu Phe
            35
```

( 2 ) INFORMATION FOR SEQ ID NO:2:

( i ) SEQUENCE CHARACTERISTICS:
        ( A ) LENGTH: 28 amino acids
        ( B ) TYPE: amino acid
        ( D ) TOPOLOGY: circular ( i i ) MOLECULE TYPE: peptide ( x i ) SEQUENCE DESCRIPTION: SEQ ID NO:2:

```
Ser Leu Arg Arg Ser Ser Cys Phe Gly Gly Arg Met Asp Arg Ile Gly
 1               5                  10                    15

Ala Gln Ser Gly Leu Gly Cys Asn Ser Phe Arg Tyr
            20                  25
```